United States Patent [19]

Sikkenga et al.

[11] Patent Number: 5,284,987
[45] Date of Patent: Feb. 8, 1994

[54] PREPARATION OF A DIMETHYLTETRALIN IN A DISTILLATION REACTOR

[75] Inventors: David L. Sikkenga; Ian C. Zaenger, both of Wheaton, Ill.; Gregory S. Williams, Tampa, Fla.

[73] Assignee: Amoco Corporation, Chicago, Ill.

[21] Appl. No.: 831,167

[22] Filed: Feb. 5, 1992

Related U.S. Application Data

[63] Continuation-in-part of Ser. No. 794,018, Nov. 19, 1991, abandoned, which is a continuation of Ser. No. 633,068, Dec. 21, 1990, abandoned, which is a continuation-in-part of Ser. No. 539,007, Jun. 15, 1990, Pat. No. 5,030,781, and Ser. No. 539,087, Jun. 15, 1990, Pat. No. 5,034,561, and Ser. No. 556,297, Jul. 20, 1990, Pat. No. 5,073,678.

[51] Int. Cl.$^5$ .............................................. C07C 5/00
[52] U.S. Cl. .................................. 585/410; 585/411; 585/430; 585/320; 585/481; 203/34; 203/DIG. 6
[58] Field of Search .............. 585/410, 411, 320, 400, 585/430, 477, 480, 481; 203/34, DIG. 6

[56] References Cited

U.S. PATENT DOCUMENTS

| | | | |
|---|---|---|---|
| 4,950,825 | 8/1990 | Sikkenga et al. | 585/320 |
| 5,030,781 | 7/1991 | Sikkenga et al. | 585/320 |
| 5,034,561 | 7/1991 | Sikkenga et al. | 585/320 |
| 5,176,683 | 1/1993 | Smith, Jr. et al. | 203/DIG. 6 |

FOREIGN PATENT DOCUMENTS 48-96577 10/1973 Japan .................................. 585/320

*Primary Examiner*—Asok Pal
*Attorney, Agent, or Firm*—Thomas E. Nemo; Wallace L. Oliver

[57] ABSTRACT

A method for the acid catalyzed cyclization of an alkenylbenzene feedstock to a dimethyltetralin in a liquid phase reaction wherein the desired dimethyltetralin is removed from the reaction mixture by distillation simultaneously with the addition of the feedstock to the reaction mixture.

8 Claims, 1 Drawing Sheet

PREPARATION OF A DIMETHYLTETRALIN IN A DISTILLATION REACTOR

RELATED APPLICATIONS

This application is a continuation-in-part of application Ser. No. 794,018, filed Nov. 19, 1991, now abandoned, which is a continuation of application Ser. No. 633,068, filed Dec. 21, 1990, now abandoned, which is a continuation-in-part of patent application Ser. No. 539,007, filed on Jun. 15, 1990, now U.S. Pat. No. 5,030,781, patent application Ser. No. 539,087, filed Jun. 15, 1990, now U.S. Pat. No. 5,034,561, and patent application Ser. No. 556,297, filed on Jul. 20, 1990, now U.S. Pat. No. 5,073,678.

FIELD OF THE INVENTION

This invention relates generally to a method for preparing a dimethyltetralin and more particularly concerns an improved method for preparing a specific dimethyltetralin or a mixture of specific dimethyltetralins by the cyclization of either 5-(o-, m-, or p-tolyl)-pent-1- or -2-ene or 5-phenyl-hex-1- or -2-ene in a liquid phase reaction.

BACKGROUND OF THE INVENTION

Naphthalene dicarboxylic acids are monomers that are known to be useful for the preparation of a variety of polymers. For example, poly(ethylene 2,6-naphthalate) prepared from 2,6-naphthalene dicarboxylic acid and ethylene glycol has better heat resistance and mechanical properties than polyethylene terephthalate and is useful in the manufacture of films and fibers.

Dimethylnaphthalenes are desirable feedstocks for oxidation to the corresponding naphthalene dicarboxylic acids. A known conventional process for producing a naphthalene dicarboxylic acid comprises the oxidation of a dimethylnaphthalene with oxygen in the liquid phase in an acetic acid solvent at an elevated temperature and pressure and in the presence of a catalyst comprising cobalt, manganese and bromine components.

Typically, dimethylnaphthalenes are found in refinery or coal-derived streams as mixtures of all of the ten possible dimethylnaphthalene isomers. However, separation of these isomers is very difficult and expensive. Consequently, methods for producing specific dimethylnaphthalenes or mixtures of two or three specific dimethylnaphthalenes in high purity and quality are highly desirable. One such method is a multistep synthesis involving: (1) the formation of an alkenylbenzene by the reaction of o-, m- or p-xylene or ethylbenzene with butadiene; (2) the cyclization of the resulting alkenylbenzene to form one or more dimethyltetralins belonging to one or two of three groups of isomeric dimethyltetralins—that is, either the group containing the 1,5-, 1,6-, 2,5- and 2,6-dimethyltetralins, the group containing the 1,7-, 1,8- 2,7- and 2,8-dimethyltetralins, or the group containing the 1,3-, 1,4-, 2,3- 5,7- 5,8- and 6,7-dimethyltetralins; (3) the dehydrogenation of the dimethyltetralin(s) to form the corresponding dimethylnaphthalene(s), and (4) the isomerization of the resulting dimethylnaphthalene(s) to the desired specific dimethylnaphthalene. The 1,5-, 1,6-, and 2,6-dimethylnaphthalenes make up the group that is commonly referred to as the Group A triad. The 1,7-, 1,8- and 2,7-dimethylnaphthalenes make up the group that is commonly referred to as the Group B triad. The 1,3-, 1,4- and 2,3-dimethylnaphthalenes make up the group that is commonly referred to as the Group C triad. In this regard, it is known that in the presence of an acid catalyst, the dimethylnaphthalene isomers are isomerizable within each triad of dimethylnaphthalene isomers—that is, within the 1,5- 1,6- and 2,6-dimethylnaphthalenes of triad A, within the 1,7- 1,8-, and 2,7-dimethylnaphthalenes of triad B, and within the 1,3-, 1,4- and 2,3-dimethylnaphthalenes of triad C. It is also known that the interconversion of a dimethylnaphthalene isomer within one of the aforesaid triads to a dimethylnaphthalene isomer within another of the aforesaid triads occurs to a relatively lesser extent.

For example, Sikkenga et al., U.S. Pat. No. 4,950,825 discloses an improved method for preparing one or more dimethyltetralins from 5-(o-, m-, or p-tolyl)-pent-1- or -2-ene or 5-phenyl-hex-1- or -2-ene as the first feedstock which comprises contacting the first feedstock in liquid form with a solid cyclization catalyst comprising an acidic, ultrastable crystalline aluminosilicate molecular sieve Y-zeolite that is substantially free of adsorbed water, and at a temperature in the range of from about 120° C. to about 350° C. and at a pressure that is sufficiently high to maintain the first feedstock substantially in the liquid phase to thereby cyclize the first feedstock to form a first liquid product comprising one or more dimethyltetralins, wherein water is at a concentration in the first feedstock of from 0.0 up to less than about 0.5 weight percent, based on the weight of the feedstock, wherein (a) when the first feedstock comprises 5-(o-tolyl)-pent-1- or -2-ene, at least 80 weight percent of the dimethyltetralin product formed is comprised of 1,5-, 1,6-, 2,5- or 2,6-dimethyltetralin or a mixture thereof, (b) when the first feedstock comprises 5-(m-tolyl)-pent-1- or -2-ene, at least 80 weight percent of the mixture of the dimethyltetralin product formed is comprised of 1,5- 1,6- 1,7-1,8- 2,5-, 2,6-, 2,7- or 2,8-dimethyltetralin or a mixture thereof, (c) when the first feedstock comprises 5-(p-tolyl)-pent-1- or -2-ene, at least 80 weight percent of the dimethyltetralin product formed is comprised of 1,7-, 1,8-, 2,7- or 2,8-dimethyltetralin or a mixture thereof, and (d) when the first feedstock comprises 5-phenyl-1- or -2-hexene, at least 80 weight percent of the dimethyltetralin product formed is comprised of 1,3-, 1,4-, 2,3-, 5,7-, 5,8- or 6,7-dimethyltetralin or a mixture thereof.

Thompson, U.S. Pat. Nos. 3,775,496; 3,775,497; 3,775,498; and 3,775,500 disclose processes for the cyclization of specific alkenylbenzenes to one or more specific dimethyltetralins at 200°–450° C. in the presence of any suitable solid acidic cyclization catalyst such as acidic crystalline zeolites as well as silica-alumina, silica-magnesia, and silica-alumina-zirconia and phosphoric acid, followed by the dehydrogenation of the resulting dimethyltetralin(s) in the vapor state to the corresponding dimethylnaphthalene(s) in a hydrogen atmosphere at 300°–500° C. and in the presence of a solid dehydrogenation catalyst such as noble metals on carriers and chromia-alumina, and thereafter isomerization of each of the aforesaid dimethylnaphthalene(s) to the desired isomer within the triad of dimethylnaphthalenes to which the isomer being isomerized belongs at 275°–500° C. in the presence of a solid acidic isomerization catalyst of the same type as described in respect of the cyclization disclosed therein. In the alternative, both the cyclization and isomerization reactions can be performed in the liquid phase, in which case the cyclization is performed at 200°–275° C. with a solid phosphoric acid catalyst, at 70°-140° C. with an acidic ion exchange resin, an acidic crystalline zeolite, hydrofluoric or sulfuric acid as the catalyst or a siliceous cracking catalyst.

More specifically, Thompson, U.S. Pat. No. 3,775,496, discloses the cyclization of 5-(m-tolyl)-pent-2-ene to 1,6- and 1,8-dimethyltetralins, which are then dehydrogenated to 1,6- and 1,8-dimethylnaphthalenes, which in turn are isomerized to 2,6- and 2,7-dimethylnaphthalenes, respectively. Thompson, U.S. Pat. No. 3,775,497, discloses the cyclization of 5-phenyl-hex-2-ene to 1,4-dimethyltetralin which is then dehydrogenated to 1,4-dimethylnaphthalene, which is in turn isomerized to 2,3-dimethylnaphthalene. Thompson, U.S. Pat. No. 3,775,498, discloses the cyclization of 5-(o-tolyl)pent-2-ene to 1,5-dimethyltetralin, which is then dehydrogenated to 1,5-dimethylnaphthalene, which is in turn isomerized to 2,6-dimethylnaphthalene. Thompson, U.S. Pat. No. 3,775,500 discloses the cyclization of 5-(p-tolyl)pent-2-ene to 1,7-dimethyltetralin, which is then dehydrogenated to 1,7-dimethylnaphthalene, which in turn is isomerized to 2,7-dimethylnaphthalene.

A problem in such prior art methods is the presence of impurities such as unconverted alkenylbenzene as well as by-products, particularly heavy, high-boiling by-products, in the cyclization reaction product. Additionally, because the cyclization reaction is exothermic, prior art processes that utilize a fixed bed of cyclization catalyst are undesirable. The fixed bed reactors can develop hot spots in the catalyst bed because the heat from the reaction cannot be rapidly dissipated. Such hot spots cause catalyst deactivation and increased formation of reaction by-products.

Consequently, it is highly desired to provide for an improved cyclization step in the aforesaid synthesis of dimethyltetralin isomers, which upon dehydrogenation are subsequently converted to dimethylnaphthalene.

OBJECTS OF THE INVENTION

It is therefor a general object of the present invention to provide an improved method for manufacturing a specific dimethyltetralin isomer or set of dimethyltetralin isomers by the cyclization of an alkenylbenzene.

It is a related object of the present invention to provide an improved method for manufacturing with an improved yield and selectivity a specific dimethyltetralin isomer or set of dimethyltetralin isomers by providing an improved method for the cyclization of an alkenylbenzene to form a specific dimethyltetralin isomer or set of dimethyltetralin isomers and eliminating undesirable, relatively heavier by-products from the cyclization product mixture.

Other objects and advantages of the method of the present invention will become apparent upon reading the following detailed description and appended claims.

SUMMARY OF THE INVENTION

The objects of the invention are achieved by an improved method for preparing one or more dimethyltetralins from 5-(o-, m-, or p-tolyl)-pent-1- or 2-ene or 5-phenyl-hex-1- or -2-ene as the alkenylbenzene feedstock, comprising: contacting the feedstock in a liquid form with an acidic cyclization catalyst in a suitable reaction zone at a temperature sufficient to provide for the cyclization of the feedstock thereby forming a reaction mixture comprising the cyclization catalyst and one or more dimethyltetralins wherein (1) when the feedstock comprises 5-(o-tolyl)-pent-1- or -2-ene, at least 80 weight percent of the dimethyltetralin product formed is comprised of 1,5-, 1,6-, 2,5- or 2,6-dimethyltetralin, (2) when the feedstock comprises 5-(m-tolyl)-pent-1- or -2-ene, at least 80 weight percent of the dimethyltetralin product formed is comprised of 1,5-, 1,6-, 1,7-, 1,8-, 2,5- 2,6-, 2,7- or 2,8-dimethyltetralin or a mixture thereof, (3) when the feedstock comprises 5-(p-tolyl)-pent-1- or -2-ene, at least 80 weight percent of the dimethyltetralin product formed is comprised of 1,7-, 1,8-, 2,7- or 2,8-dimethyltetralin or a mixture thereof, and (4) when feedstock comprises 5-phenyl-1- or -2-hexene, at least 80 weight percent of the dimethyltetralin product formed is comprised of 1,3-, 1,4-, 2,3-, 5,7-, 5,8- or 6,7-dimethyltetralin or a mixture thereof; and removing by distillation from the reaction mixture a lighter fraction comprising the dimethyltetralin product, wherein the distillation is conducted simultaneously with the addition of the feedstock to the reaction mixture.

DETAILED DESCRIPTION OF THE PREFERRED EMBODIMENTS

Figure 1:
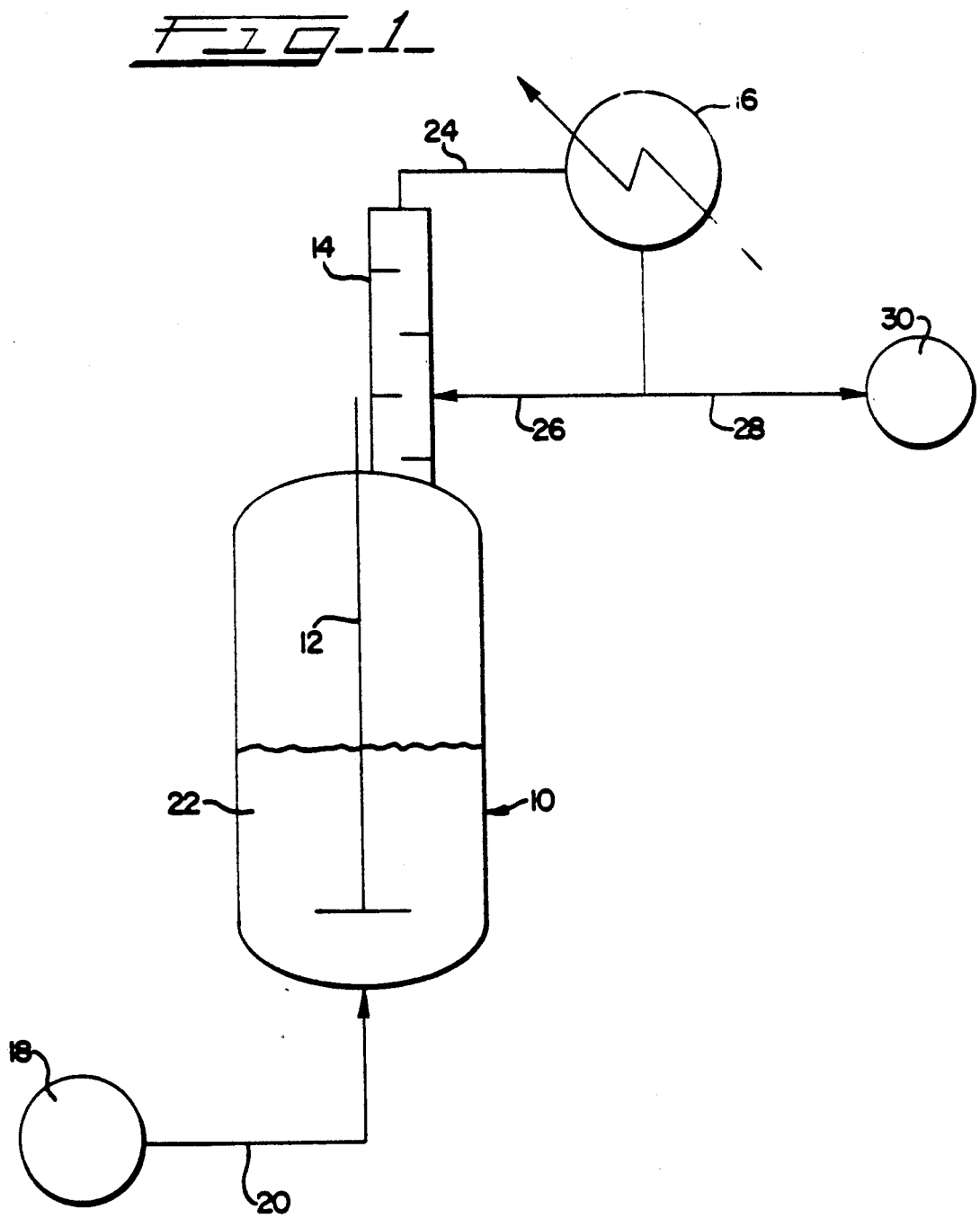
FIG. 1 is a schematic flow diagram illustrating the continuous cyclization method of this invention.

Suitable feedstocks for use in the cyclization method of the present invention are the alkenylbenzenes 5-(o-, m-, or p-tolyl)-pent-1- or -2-ene, or 5-phenyl-hex-1- or -2-ene. In the typical context in which the method of the present invention is employed, the dimethyltetralin product of the cyclization method of this invention is subsequently dehydrogenated to form one or more dimethylnaphthalenes which are then isomerized to the desired dimethylnaphthalene.

When 5-(o-tolyl)-pent-1- or -2-ene is the feedstock to the cyclization step of the present invention, 1,5-, 1,6-, 2,5-, or 2,6-dimethyltetralin or a mixture thereof comprises at least 80, preferably at least 85, weight percent of the dimethyltetralin product produced therefrom, which resulting dimethyltetralin product is in turn the feedstock and is converted in the aforesaid dehydrogenation step to the corresponding 1,5- 1,6- and 2,6-dimethylnaphthalenes, which are then the feedstock in the aforesaid isomerization step, wherein 1,5- and 1,6-dimethylnaphthalene therein are substantially converted to 2,6-dimethylnaphthalene.

When 5-(m-tolyl)-pent-1- or -2-ene is the feedstock to the cyclization step of the method of this invention, 1,5- 1,6- 1,7-, 1,8- 2,5- 2,6-, 2,7- or 2,8-dimethyltetralin or a mixture thereof comprises at least 80, preferably at least 85, weight percent of the dimethyltetralin product produced therefrom, which dimethyltetralins are in turn the feedstock and are converted in the aforesaid dehydrogenation step to the corresponding 1,5-, 1,6-, 1,7-, 1,8- 2,6- and 2,7-dimethylnaphthalenes, which are then the feedstock in the aforesaid isomerization step, wherein the 1,5-, 1,6-, 1,7- and 1,8-dimethylnaphthalenes therein are substantially converted to 2,6- and 2,7-dimethylnaphthalenes.

When 5-(p-tolyl)-pent-1- or -2-ene is the feedstock to the cyclization step of the method of this invention, 1,7-, 1,8-, 2,7- or 2,8-dimethyltetralin or a mixture thereof comprises at least 80, preferably at least 85, weight percent of the dimethyltetralin product produced therefrom, which dimethyltetralins are in turn the feedstock and are converted in the aforesaid dehydrogenation step to the corresponding 1,7-, 1,8- and 2,7-dimethylnaphthalenes, which are then the feedstock in the aforesaid isomerization step, wherein the 1,7- and 1,8-dimethylnaphthalenes therein are substantially converted to 2,7-dimethylnaphthalene.

When 5-phenyl-1- or -2-hexene is the feedstock to the cyclization step of the method of this invention, 1,3-, 1,4-, 2,3-, 5,7-, 5,8-, or 6,7-dimethyltetralin or a mixture thereof comprises at least 80, preferably at least 85, weight percent of the dimethyltetralin product produced therefrom, which dimethyltetralins are in turn the feedstock and are converted in the aforesaid dehydrogenation step to the corresponding, 1,3-, 1,4- and 2,3-dimethylnaphthalenes, which are then the feedstock in the aforesaid isomerization step, wherein the 1,3- and 1,4-dimethylnaphthalenes therein are substantially converted to 2,3-dimethylnaphthalene.

In the cyclization method of the present invention, the reaction is performed in the liquid phase at an elevated temperature and at a pressure sufficient to ensure that the 5-(o-, m-, or p-tolyl)-pent-1- or -2-ene or 5-phenylhex-1-or -2-ene cyclization feedstock is maintained substantially in the liquid phase. The cyclization reaction is performed at a temperature in the range of from about 90° C., preferably from about 120° C., to about 420° C., preferably to about 350° C., and generally at a pressure in the range of from about 0.05, preferably from about 0.1 to about 10, preferably to about 1.3 atmospheres absolute. Most preferably, the cyclization reaction is performed at a temperature of from about 150° C. to about 300° C.

The cyclization reaction can be performed with or without a solvent for the feedstock. Preferably a solvent is not employed. If employed, a solvent must be inert under the conditions employed and suitably comprises a paraffin, such as a tetradecane, or an aromatic hydrocarbon, such as a anthracene, or mixtures thereof, which preferably boil above about 270° C. In the cyclization step, if water is present, its concentration must be less than 0.5 weight percent, preferably less than 0.1 weight percent, based on the weight of the alkenylbenzene feedstock. More preferably, water is not present in the cyclization reaction medium.

In the cyclization method of this invention, the alkenylbenzene feedstock comprising 5-(o-, m-, or p-tolyl)-pent-1- or -2-ene or 5-phenyl-hex-1- or 2-ene is continuously added to a suitable reaction zone, such as a stirred tank reactor, containing a cyclization catalyst, the desired cyclization reaction occurs and a product mixture comprising the desired dimethyltetralin is simultaneously removed from the reaction mixture by distilling the dimethyltetralin directly from the reaction mixture which comprises the desired dimethyltetralin. Heavy materials produced during the acid catalyzed cyclization reaction, e.g. high boiling reaction by-products, and the cyclization catalyst remain mainly in the reaction mixture.

In the method of this invention, the cyclization catalyst is dispersed in the reaction mixture. For example, if a solid cyclization catalyst is used, it is used in the form of particles. Consequently, the reaction mixture comprises a slurry of the solid particulate catalyst in the reaction mixture. Because the cyclization reaction is exothermic, the dispersion of the catalyst in the reaction mixture eliminates the formation of localized hot spots that would form if a fixed catalyst bed were used. Additionally, because the reaction product is distilled directly from the reaction mixture, the cyclization reaction can be conducted with excellent heat control whereby the temperature of the reaction is regulated so that it does not go higher than essentially the reflux temperature of the reaction mixture and, furthermore, the heat generated by the cyclization reaction assists in the distillation of the dimethyltetralin product.

The catalyst employed in the cyclization method of this invention comprises an acidic catalyst having sufficient acidity to cyclize the 5-(o-, m, or p-tolyl)-pent-1- or -2-ene or 5-phenyl-hex-1- or -2-ene to the specific dimethyltetralin. Preferably, the acidic cyclization catalyst is non-volatile under the reaction conditions, and most preferably it is a solid, non-volatile catalyst. For example, suitable acidic catalysts include silicalite catalysts, zeolite beta, acidic ion exchange resins such as Amberlyst-15 TM, borosilicate molecular sieves, low alumina Mordenite molecular sieves, Y molecular sieves, X molecular sieves, ZSM-5 molecular sieve, phosphoric acid, and silica-aluminas. Additionally, any of the molecular sieves mentioned above can be partially exchanged with a Group IA and IIA metal. Most preferably, the catalyst employed in the cyclization method of this invention comprises an acidic, ultrastable—that is, a thermally stabilized or dealuminated—crystalline aluminosilicate Y-zeolite having a silica-to-alumina bulk molar ration in the range of from about 3:1, preferably from about 12:1, to about 200:1, preferably to about 100:1, having pore windows provided by twelve-membered rings containing oxygen and a unit cell size in the range of from about 24.0, preferably from about 24.1, to about 24.7, preferably to about 24.3 angstroms, having a sodium content of from about 0.01 to about 0.4 weight percent, calculated as elemental sodium and based on the weight of the zeolite, and or reported in terms of the sodium oxide-to-alumina bulk molar ratio of from about 0.001:1 to about 1:1.

The term "relatively low acidity" as used herein in reference to a zeolite useful for the practice of this invention has reference to the relatively few Brønsted acid sites in the crystalline zeolite framework that provide sufficient acidity to catalyze the desired cyclization but without the production of undesirably large amounts of by-products. Substances that owe their acidity to the presence of protons are termed Brønsted acids. In the case of crystalline aluminosilicates or zeolites, a Brønsted acid site occurs in the crystalline zeolite framework where an aluminum atom surrounded by four oxygen atoms is present. Inasmuch as some of such Brønsted acid sites are neutralized by alkali metal present in the crystalline framework, the Brønsted acidity of a particular zeolite can be delineated by specifying the framework molar ratios of silica-to-alumina and sodium oxide-to-alumina as set forth herein. In terms of the number of framework Brønsted acid sites per unit cell of the crystalline zeolite catalyst, for the purposes of the present method the preferred zeolite catalyst has an average of no more than 10 framework Brønsted acid sites, preferably no more than about 4 such sites, per unit cell.

The term "ultrastable" as used herein in reference to a zeolite has reference to a zeolite which has been thermally stabilized or dealuminated to produce a synthetic zeolite having much improved resistance to degradation under acid and hydrothermal conditions. The term "zeolite Y" as used herein in reference to the contemplated crystalline aluminosilicate molecular sieve has reference to a zeolite which has the characteristic framework structure of the faujasite mineral class. The term "bulk molar ratio" as used herein denotes the molar ratio of the designated moieties regardless of whether present in the crystalline framework of the molecular sieve or not.

One type of catalyst that is suitable for use in the method of this invention as the cyclization catalyst is disclosed in Sikkenga et al., U.S. Pat. No. 4,950,825, and is an acidic, ultrastable Y zeolite catalyst in the hydrogen form having a unit cell size in the range of from about 24.2 to about 24.7 Anstroms, a silica-to-alumina molar ratio in the range of from about 4:1 to about 10:1 and a sodium content of from about 0.05 to about 3.5 weight percent, calculated as elemental sodium. Commercially available examples of this type of catalyst are LZ-Y72 and LZ-Y20, both marketed by UOP and both in powder form. In one embodiment, this zeolite optionally contains from about 0.01, more preferably from about 0.05, to about 3.0, preferably to about 1.5, weight percent of a component comprising a first metal selected from the group consisting of platinum, palladium, iridium and rhodium, calculated as the elemental metal and based on the weight of the catalyst. Suitably, this metal component comprises platinum. In this same embodiment, the catalyst can optionally also contain from about 0.01, preferably from about 1, to about 5, preferably to about 3, weight percent of a component comprising a second metal selected from the group consisting of copper, tin, gold, lead and silver, calculated as the elemental metal and based on the weight of the catalyst. Suitably, this second metal component comprises copper, tin or gold.

A most preferred type of catalyst for use as the cyclization catalyst in the method of this invention is another ultrastable zeolite Y in the hydrogen form and having a relatively low acidity that has relatively lower alumina and sodium oxide contents. The catalyst framework alumina concentration for such zeolite is indicated in part by the unit cell size which, as measured by x-ray diffraction, is no more than 24.3 Angstroms. The silica-to-alumina bulk molar ratio is at least about 12:1 and preferably at least about 30:1. The sodium oxide-to-alumina bulk molar ratio is in the range of from about 0.001:1, preferably from about 0.01:1, to about 1:1, preferably to about 0.05:1. The sodium content of this zeolite is less than about 0.4, preferably less than about 0.23 weight percent, based on the weight of the zeolite and calculated as elemental sodium. A commercially available example of this type of preferred zeolite is Valfor CP 301-26 from PQ Corporation, Valley Forge, Pa. Valfor CP 301-26 has a sodium oxide-to-alumina bulk molar ratio of about 0.02:1, a silica-to-alumina bulk molar ratio of about 80:1, a sodium content of about 0.02 weight percent based on the weight of the zeolite and calculated as elemental sodium, a unit cell size of 24.25 Angstroms, and a specific surface area of about 775 square meters per gram, and is also in powder form.

The solid catalysts used in the method of the present invention are preferably in a powdered form, a granular form or in any other finely divided form. A powdered catalyst is conveniently mechanically dispersed by mixing action in the liquid phase reactant employed. When in a granular form, the granule size can vary widely, such as from about 0.03-inch to about 1 inch in average maximum diameter, the exact size in any given instance being influenced by the choice of particular reactor. As used herein, the term "granular form" is generic to porous structures having various possible physical shapes, and made by various possible preparation methods, and such term is inclusive of both supported and unsupported catalyst forms.

The catalyst can be employed either unsupported or supported on a porous refractory, inorganic oxide that is inert under the conditions employed, such as silica, alumina, magnesia, bentonite or other such clays. If a support is employed, preferably the support comprises silica or alumina. When a support is employed, the active catalyst comprises from about 10, preferably from about 20, to about 90, preferably to about 80, weight percent based on the combined weight of the catalyst and support material.

A zeolite catalyst, when used, is preferably substantially free of adsorbed water. If present on the zeolite, the adsorber water can be removed from the zeolite by heating it in a dry atmosphere at about 250° C. for 0.5–1 hour. In the alternative, and less preferably, the presence of adsorbed water at a concentration of up to 15 weight percent of the catalyst can be tolerated if a reaction temperature of at least about 180° C. is employed.

Suitably, the addition of the alkenylbenzene feedstock to the reaction zone is such that the space velocity is in the range of about 0.1, preferably about 1, to about 100, preferably to about 50 parts of alkenylbenzene feedstock per part of active component of the cyclization catalyst, by weight, per hour.

In general, the quantity of the catalyst employed in a reaction zone for cyclization is that sufficient to be catalytically effective. Catalyst concentration can be varied to optimize the reaction rate. Concentrations of the catalyst in the range of about 0.1 to about 10 weight percent based on total reactor charge are presently preferred, with a catalyst concentration in the range of about 0.3 to about 2 weight percent being more preferred; however, larger and smaller amounts of the catalyst can be employed, if desired.

Under conditions at which the cyclization reaction is substantially complete, the resulting cyclization product mixture is separated by distillation from the reaction mixture containing the cyclization catalyst, preferably at reduced pressure, into a relatively lighter (or lower boiling) fraction that contains the dimethyltetralin product leaving in the reaction mixture relatively heavier (or high boiling) fraction that boils above the boiling point(s) of the dimethyltetralin product. The reduced pressure is preferably in the range of from about 0.03 up to less than about 1.0 atmosphere. In a preferred embodiment of the method of this invention, either immediately after the cyclization or at least ultimately, the lighter fraction which is the distillate is dehydrogenated such that the dimethyltetralins therein are converted to the corresponding dimethylnaphthalenes.

The heavier fraction of the cyclization product mixture, which is the distillation bottom, remains in the cyclization reactor or is recycled to it, and is combined with the fresh supply of the toly-pentene(s) or phenyl-hexene(s) employed as the feedstock in the aforesaid cyclization step.

Preferably, the dimethyltetralin product distilled from the reaction zone contains less than about 5 weight percent and, more preferably, less than about 1 weight percent alkenylbenzene feedstock. Variables such as the activity of the cyclization catalyst, amount of catalyst in the reaction mixture, reaction residence time and rate of addition of feedstock to the reaction zone can be adjusted to provide for a distilled product that contains the hereinabove described levels of alkenylbenzene feedstock.

We have also found that when using the preferred zeolite catalyst of this invention, heavy by-products produced during the cyclization reaction are converted or "cracked" to useful dimethyltetralins. Thus, after a period of time the concentration of heavy by-products builds up to a certain level and remains at that level for an extended period. This is advantageous because it greatly reduces the need to eliminate part of the reactor bottoms in a purge stream, and it provides for a higher yield of the desired dimethyltetralins.

A preferred embodiment of the method of this invention is schematically illustrated in FIG. 1. Reactor 10 is equipped with agitator 12, column 14 and overhead condenser 16. Alkenylbenzene feedstock from an appropriate source 18 is continuously fed via line 20 to reactor 10 that is maintained at steady state reflux conditions containing a boiling liquid admixture 22 of reactants and reaction products together with the cyclization catalyst suspended therein. The relatively lower boiling feedstock is introduced into the reactor below the liquid level therein while the cyclized product is continuously withdrawn from the reactor 10 via column 14 and is conveyed to overhead condenser 16 via line 24. The withdrawn product is condensed in condenser 16 and a portion thereof is returned to reactor 10 by means of reflux line 26 while the remainder is transported to product storage 30 via product line 28.

It is to be understood that although it is preferable to distill the desired dimethyltetralin product directly from the reaction vessel containing the cyclization reaction mixture, it is not necessary to conduct the method of this invention in such a manner. For example, the cyclization reaction can be conducted in a first vessel at predetermined reaction conditions such as a selected reaction temperature and selected reaction pressure, and the distillation of the desired product from the reaction mixture can take place from a separate vessel operating at either the same or different pressure and/or temperature. The bottoms from the second vessel containing the heavier, high-boiling components and cyclization catalyst can be recycled to the first vessel. Also, when the desired dimethyltetralin product is removed from the reaction mixture by distillation, the distillation can be conducted using a column such as that shown in FIG. 1, or, alternatively, no column is used and the distillation is conducted as a simple distillation, or flash distillation. Preferably, however, a distillation column is used to obtain efficient separation of the desired dimethyltetralin product from the heavier, higher boiling components. Preferably, the column contains packing or trays to increase further its efficiency.

The specifications of U.S. patent applications Ser. Nos. 539,007, filed on Jun. 15, 1990; 539,087, filed on Jun. 15, 1990 and 556,297, filed on Jul. 20, 1990, are specifically incorporated by reference herein.

The present invention will be more clearly understood from the following specific examples. These examples are not intended to limit the scope of the invention.

EXAMPLE I

In Example I, 32 parts by weight of crude 1,5-dimethyltetralin (1,5-DMT) and 0.96 parts by weight of UOP's LZ-Y72 catalyst were introduced into a reactor, and the contents of the reactor were heated in the first run to the desired reaction temperature of 182° C., and 5-o-tolyl-pentene-2 (OTP) was introduced into the reactor slowly over a 2-hour period in order to allow removal of the exothermal heat and maintenance of good temperature control. A total of 48 parts of 5-o-tolyl-pentene-2 was added. The pressure was adjusted so as to maintain the reactants at their boiling point in the liquid phase. When the cyclization reaction was substantially complete and at least 99 weight percent of the 5-o-tolyl-pentene-2 had reacted, the reactor pressure was reduced to 2-4 psia. and the dimethyltetralin components of the product mixture were removed by low pressure distillation. The higher boiling materials and catalyst remained in the reactor as residue from the first run.

In the second run, the procedure of the first run was repeated, except that the higher boiling residue from the previous run was used instead of the crude 1,5-DMT and no additional catalyst was introduced. In each of the third, fourth and fifth runs, the procedure of the second run was repeated. The overall combined composition of the feedstocks employed in the five runs is indicated in Table I. The lower boiling products withdrawn as distillates in the five runs were combined, and the composition of this combination is also indicated in Table I. The higher boiling product remaining in the reactor as residue from the fifth run was analyzed, and its composition is also reported in Table I. This residue from the fifth run and distillation was then subjected to cracking under the same conditions and treatment employed in the fifth run, except that a reaction temperature of 250°-260° C. was employed and no 5-o-tolyl-pentene-2 was added. The cracked products boiling below the cracking temperature were removed by low pressure distillation as the "final distillate," and its composition is reported in Table I. The higher boiling products remained in the reactor as the "final residue.", and its composition is also reported in Table I. The overall composition of the total of the distillates from the five runs and the final distillate from the fifth distillation residue is reported in Table I as the combined 6 Distillates.

The results of Example I illustrate clearly that the distillation overhead which contains the dimethyltetralins (DMTs) and serves as the feedstock for the subsequent dehydrogenation to form dimethylnaphthalenes (DMNs) contains essentially no detectable heavies. Also, since the cyclization catalyst is not separated from the heavy distillation bottoms and is recycled to the cyclization step with this heavy fraction, there are no losses of catalyst due to filtration or other separation of the catalyst. The cracking step also reduces the total amount of unuseful distillation residue from 5:11 weight percent to 1.25 weight percent of the total product and therefore increases the absolute amount of useful DMTs and DMNs produced in the cyclization reaction.

TABLE 1

| Components | Composition | | | | | |
|---|---|---|---|---|---|---|
| | | | 5th Distillation Residue | Products from Cracking and Distillation of 5th Distillation Residue | | |
| | Combined 5 Feedstocks | Combined 5 Distillates | | Final Distillate | Final Residue | Combined 6 Distillates |
| OTP | 88.59 | 1.37 | 0 | 0 | 0 | 1.3 |
| Saturated OTP | 0.56 | 4.10 | 0 | 6.60 | 0 | 4.2 |
| Unknown DMT | 0.16 | 1.29 | 0 | 5.10 | 0 | 1.4 |
| 1,6-DMT | 0.27 | 3.20 | 0.28 | 10.80 | 0 | 3.5 |
| 2,5-DMT | 0.06 | 1.40 | 0.26 | 8.6 | 0 | 1.7 |
| 1,5-DMT | 9.54 | 83.81 | 11.1 | 8.9 | 0 | 80.9 |
| 1,6-DMN | 0.03 | 0.41 | 0.36 | 3.3 | 0 | 0.5 |
| 1,5-DMN | 0.28 | 1.87 | 1.67 | 0.9 | 0 | 1.9 |
| Heavies | 0.51 | 0.06 | 83.5 | 1.00 | 100.0 | 0.1 |
| Other | 0.30 | 2.49 | 2.83 | 54.76 | 0 | 4.5 |
| Total useful DMTs and DMNs | 10.18 | 40.68 | 13.67 | 32.54 | 0 | 88.5 |
| Total | 100.00 | 100.00 | 100.00 | 100.00 | 100.00 | 100.00 |
| Percent of total product | — | 94.89 | 5.11 | 3.86 | 1.25 | 98.75 |

EXAMPLES 2-9

Each of Examples 2-9 was performed batchwise. In Example 2, 150 grams of 5-o-tolyl-pentene-2 and 1.80 grams of the particular solid cyclization catalysts employed were charged to a reactor equipped with a reflux condenser and distillation/collection head, and the reactor was evacuated to the desired reaction pressure. The reactor contents were then heated to the reaction temperature, at which point the reactor contents were at reflux. The pressure was controlled to maintain the reactants in the liquid phase. When at least 99 weight percent of the 5-o-tolyl-pentene-2 was converted, as indicated by gas chromatographic measurement, the reaction time was noted, and the temperature of the reactor contents was gradually reduced, and the pressure was gradually increased to atmospheric pressure. No product was distilled out of or removed from the reactor. When cooled, the reactor contents included the cyclization product mixture and solid catalyst employed, and a 1.8 gm sample of the product mixture was withdrawn for analysis.

In Example 3, the entire product mixture and catalyst from Example 2 was returned to the reactor as the heel for the next batch of 5-o-tolyl-pentene-2. Additional solid cyclization catalyst was added to this heel, and the reactor was heated under reduced pressure to obtain reflux at the desired reaction temperature in the liquid state. A portion of 5-o-tolyl-pentene-2 was then gradually added to the reaction mixture over a period of 2 hours to allow removal of the exothermic heat and maintenance of good temperature control. Unlike Example 2, at the end of the reaction time—that is, when at least 99 weight percent of the 5-o-tolyl-pentene-2 has reacted—as indicated by gas chromatographic analysis, the pressure is slowly reduced to 2.4 pounds per square inch absolute, and slowly the temperature was decreased to below the reaction temperature in order to flash distill the lighter or lower boiling fraction containing the dimethyltetralin products. The products that distilled were collected outside the reactor and analyzed. The solid catalyst and heavy products remaining in the reactor constituted approximately 25 weight percent of total cyclization product mixture. The heavy products and catalyst remaining in the reactor served as the heel for the next run, as described below.

In each of Examples 4-9, to the heel (including the catalyst) from the previous example, using the procedure of Example 3, a portion of 5-o-tolyl-pentene-2, but no additional solid catalyst was added, and the reactor contents were heated and maintained under vacuum to allow reflux. At the completion of the cyclization reaction, the reactor pressure was reduced further, and the lighter products were flash distilled, collected and analyzed, and the heavy products and catalyst remaining in the reactor were employed as the heel for the next run (Example), also as described for Example 3. The catalyst employed in Examples 2-9 was Conteka CBV 760.

The conditions employed and results from Examples 2-9 are presented in Tables 2-3.

EXAMPLES 10-17

Example 10 was performed using the same general procedure employed in Example 2 and the product mixture produced in Example 10 served as the heel for Example 11. Examples 11-17 were performed using the same general procedures of Examples 3-9. The catalyst employed in Examples 10-17 was UOP's LZ-Y72. The conditions employed in, and the results from, Examples 10-17 are presented in Tables 4-5.

EXAMPLE 18

In Example 18, for the run on the first day of operation 8.83 grams of Conteka 760 catalyst and 440 grams of a liquid reaction medium were introduced into a 1000-milliliter stirred tank reactor which was maintained at the desired reaction temperature and which was fitted with the overhead distillation column connected to a vacuum system. The reactor pressure was reduced to 0.2 to 0.3 atmosphere in order to achieve reflux at the desired reaction temperature, and then liquid 5-0-tolyl-2-pentene (OTP) was passed continuously through the liquid reaction medium in the reactor, and reaction product passed continuously upward into the distillation column. The portion of the reaction product boiling below about 265° C. (at 1 atmosphere pressure) was continuously withdrawn as overhead from the distillation column, and the higher boiling fractions were either returned to the reactor as distillation bottoms or never vaporized or passed into the distillation column.

A run for a particular day was concluded by discontinuing the flow of OTP into the reactor, cooling the reactor contents to room temperature, raising the reactor pressure to one atmosphere while purging the reactor with nitrogen in order to eliminate oxygen. To begin the next day's run, the reactor was heated to the desired reaction temperature, reactor pressure was reduced to 0.2–0.3 atmosphere in order to bring the reactor contents to reflux and then liquid OTP was again passed into the reactor, and into the heavy liquid reaction product that boiled above 265° C. (at 1 atmosphere pressure) and that remained in the reactor from the previous day's run, but without the introduction of additional catalyst or liquid reaction medium.

TABLE 2

|  | Example 2 | Example 3 | Example 4 | Example 5 | Example 6 | Example 7 | Example 8 | Example 9 |
|---|---|---|---|---|---|---|---|---|
| Heel wt. (g) | — | 148.2 | 171.6 | 179.1 | 206.0 | 204.8 | 199.6 | 197.6 |
| Liquid Wt. (g) | — | 146.4 | 164.4 | 171.9 | 198.8 | 197.6 | 192.4 | 190.4 |
| Catalyst wt. (g) | — | 1.8 | 7.2 | 7.2 | 7.2 | 7.2 | 7.2 | 7.2 |
| OTP wt. (g) | 150 | 448 | 450 | 439 | 420 | 450 | 441 | 451 |
| Added catalyst wt. (g) | 1.8 | 5.4 | 0 | 0 | 0 | 0 | 0 | 0 |
| Total catalyst weight (g) | 1.8 | 7.2 | 7.2 | 7.2 | 7.2 | 7.2 | 7.2 | 7.2 |
| Reaction temperature (°C.) | 180 | 180 | 180 | 180 | 180 | 180 | 180 | 180–200 |
| Reaction pressure (psia) | 2–4 | 2–4 | 2–4 | 2–4 | 2–4 | 2–4 | 2–4 | 2–4 |
| Reaction time (hrs.) | 3 | <2 | <2 | <2 | <2 | <2 | <2 | <2 |
| Reduced pressure (psia) | — | 1–2 | 1–3 | 2–3 | 2–3 | 2–3 | 2–3 | 2–3 |
| Distilled product wt. (g) | 1.8* | 431.8 | 442.5 | 412.1 | 421.2 | 455.2 | 443.0 | 444.7 |
| Residual product wt. (g) | 148.2 | 164.4 | 171.9 | 198.8 | 197.6 | 192.4 | 190.4 | 186.7 |

*a 1.8 g sample of the undistilled total 148.2 g residual product reactor contents

TABLE 3

| | Composition of Distilled Product Removed From Reactor (Wt. %) | | | | | | | |
|---|---|---|---|---|---|---|---|---|
| Components | Example 2* | Example 3 | Example 4 | Example 5 | Example 6 | Example 7 | Example 8 | Example 9 |
| OTP | 0.2 | 0.0 | 0.0 | 0.1 | 0.0 | 0.1 | 0.1 | 0.0 |
| saturated OTP | 1.9 | 3.1 | 2.0 | 2.0 | 2.2 | 1.8 | 2.1 | 2.2 |
| unknown DMT isomers | 0.5 | 0.5 | 0.4 | 0.4 | 0.4 | 0.4 | 0.4 | 0.5 |
| 2,6-, 2,7-, and 1,7-DMT | 0.1 | 0.1 | 0.1 | 0.1 | 0.1 | 0.1 | 0.1 | 0.1 |
| 1,6-DMT | 0.5 | 0.5 | 0.7 | 0.7 | 0.8 | 0.7 | 0.7 | 1.0 |
| 2,8-DMT | 0.8 | 0.8 | 0.8 | 0.8 | 0.8 | 0.8 | 0.9 | 0.8 |
| 2,5-DMT | 0.1 | 0.2 | 0.3 | 0.3 | 0.4 | 0.3 | 0.3 | 0.4 |
| 1,5-DMT | 87.3 | 93.1 | 94.1 | 93.9 | 93.4 | 93.7 | 93.5 | 93.1 |
| 2,6-, 2,7-DMN | 0.0 | 0.0 | 0.0 | 0.0 | 0.0 | 0.0 | 0.0 | 0.0 |
| 1,7-DMN | 0.0 | 0.0 | 0.0 | 0.0 | 0.0 | 0.0 | 0.0 | 0.0 |
| 1,6-DMN | 0.0 | 0.0 | 0.0 | 0.0 | 0.1 | 0.1 | 0.1 | 0.1 |
| 1,5-DMN | 0.8 | 0.7 | 1.0 | 1.1 | 1.1 | 1.3 | 1.1 | 1.0 |
| 1.8-DMN | 0.0 | 0.0 | 0.0 | 0.0 | 0.0 | 0.0 | 0.0 | 0.0 |
| Heavies | 3.4 | 0.0 | 0.1 | 0.1 | 0.1 | 0.1 | 0.2 | 0.2 |
| Unknown | 2.5 | 0.2 | 0.2 | 0.2 | 0.2 | 0.2 | 0.2 | 0.2 |
| Total useful DMTs | 88.0 | 94.1 | 95.2 | 94.9 | 94.7 | 94.8 | 94.5 | 94.6 |
| Total useful DMNs | 0.8 | 0.7 | 1.0 | 1.1 | 1.1 | 1.3 | 1.1 | 1.0 |
| Total useful products | 88.8 | 94.8 | 96.2 | 96.0 | 95.8 | 96.1 | 95.6 | 95.6 |
| Total products | 100 | 100 | 100 | 100 | 100 | 100 | 100 | 100 |
| Parts of Distilled Products per 100 parts of OTP feedstock (including Ex2) | | | | | | | | |
| Total useful products | — | 68.7 | 79.8 | 82.8 | 85.7 | 87.9 | 89.2 | 89.9 |
| Total major by-products Saturated OTP | — | 2.2 | 2.1 | 2.0 | 2.1 | 2.0 | 2.0 | 2.1 |
| 2,7-Triad DMTs | — | 0.7 | 0.7 | 0.8 | 0.8 | 0.8 | 0.8 | 0.8 |
| Unknown DMT isomers | — | 0.4 | 0.4 | 0.4 | 0.4 | 0.4 | 0.4 | 0.4 |
| Unknowns | — | 0.1 | 0.1 | 0.1 | 0.2 | 0.2 | 0.2 | 0.2 |
| Heavies | — | 0.0 | 0.0 | 0.1 | 0.1 | 0.1 | 0.1 | 0.1 |

*the composition of the undistilled total reaction product remaining in the reactor

TABLE 4

|  | Example 10 | Example 11 | Example 12 | Example 13 | Example 14 | Example 15 | Example 16 | Example 17 |
|---|---|---|---|---|---|---|---|---|
| Heel wt. (g) | — | 149.0 | 156.7 | 142.5 | 194.6 | 181.6 | 187.6 | 202.3 |
| Liquid wt. (g) | — | 147.2 | 149.5 | 135.3 | 187.4 | 174.4 | 180.4 | 195.1 |
| Catalyst wt. (g) | — | 1.8 | 7.2 | 7.2 | 7.2 | 7.2 | 7.2 | 7.2 |
| OTP wt. (g) | 150 | 440 | 440 | 440 | 403 | 417 | 420.6 | 406.6 |
| Added catalyst wt. (g) | 1.8 | 5.4 | 0.0 | 0.0 | 0.0 | 0.0 | 0.0 | 0.0 |
| Total Catalyst weight (g) | 1.8 | 7.2 | 7.2 | 7.2 | 7.2 | 7.2 | 7.2 | 7.2 |
| Reaction temperature (°C.) | 190 | 190 | 200 | 216 | 237 | 238 | 238 | 238 |
| Reaction | 4–5 | 4–5 | 5–6 | 10–12 | 14.7 | 14.7 | 14.7 | 14.7 |

TABLE 4-continued

|  | Example 10 | Example 11 | Example 12 | Example 13 | Example 14 | Example 15 | Example 16 | Example 17 |
|---|---|---|---|---|---|---|---|---|
| pressure (psia) |  |  |  |  |  |  |  |  |
| Reaction time (hrs.) | 4.5 | 4.0 | 7.0 | 8.0 | 2.8 | 2.8 | 2.8 | 2.8 |
| Reduced pressure (psia) | — | 1-2 | 1-2 | 1-2 | 1-2 | 1-2 | 1-2 | 1-2 |
| Distilled product wt. (g) | 2.8* | 437.7 | 454.2 | 387.9 | 415.6 | 411.4 | 405.6 | 391.4 |
| Residual product wt. (g) | 147.2 | 149.5 | 135.3 | 187.4 | 174.8 | 180.4 | 195.1 | 210.3 |

*a 2.8 g sample of the undistilled total 147.2 residual product reactor contents

TABLE 5

| | Composition of Distilled Products Removed from Reactor (wt. %) | | | | | | | |
|---|---|---|---|---|---|---|---|---|
| Components | Example 10* | Example 11 | Example 12 | Example 13 | Example 14 | Example 15 | Example 16 | Example 17 |
| o-xylene | 0.1 | 0.1 | 0.1 | 0.2 | 0.3 | 0.2 | 0.2 | 0.2 |
| OTP | 0.3 | 0.1 | 0.3 | 0.1 | 0.2 | 0.1 | 0.1 | 0.1 |
| saturated OTP | 2.5 | 4.4 | 2.8 | 3.9 | 5.0 | 4.9 | 4.7 | 4.7 |
| Unknown DMT isomers | 0.9 | 1.2 | 1.0 | 1.3 | 1.8 | 1.8 | 1.8 | 1.7 |
| 2,6-, 2,7-, 1,7-DMT | 0.2 | 0.2 | 0.2 | 0.3 | 0.5 | 0.4 | 0.4 | 0.4 |
| 1,6-DMT | 0.9 | 0.9 | 0.9 | 1.2 | 2.5 | 2.3 | 1.9 | 1.9 |
| 2,8-DMT | 0.8 | 0.9 | 0.9 | 0.8 | 0.8 | 0.8 | 0.9 | 0.9 |
| 2,5-DMT | 0.3 | 0.3 | 0.4 | 0.6 | 0.9 | 0.8 | 0.7 | 0.8 |
| 1,5-DMT | 85.8 | 90.0 | 89.8 | 89.0 | 84.6 | 85.3 | 86.1 | 86.4 |
| 2,6-, 2,7-DMN | 0.0 | 0.0 | 0.0 | 0.0 | 0.0 | 0.0 | 0.0 | 0.0 |
| 1,7-DMN | 0.0 | 0.0 | 0.0 | 0.0 | 0.0 | 0.0 | 0.0 | 0.0 |
| 1,6-DMN | 0.1 | 0.0 | 0.1 | 0.1 | 0.3 | 0.3 | 0.3 | 0.2 |
| 1,5-DMN | 1.3 | 1.1 | 1.6 | 1.6 | 2.2 | 2.2 | 2.2 | 2.0 |
| 1,8-DMN | 0.0 | 0.0 | 0.1 | 0.0 | 0.0 | 0.0 | 0.0 | 0.0 |
| Heavies | 4.6 | 0.0 | 0.1 | 0.0 | 0.0 | 0.0 | 0.1 | 0.0 |
| Unknown | 0.8 | 0.2 | 0.6 | 0.3 | 0.2 | 0.1 | 0.1 | 0.1 |
| Total useful DMTs | 86.9 | 91.2 | 91.1 | 90.7 | 88.1 | 87.5 | 88.7 | 89.0 |
| Total useful DMNs | 1.4 | 1.1 | 1.7 | 1.7 | 2.5 | 2.5 | 2.5 | 2.2 |
| Total useful products | 88.3 | 92.3 | 92.8 | 92.4 | 90.6 | 90.0 | 91.2 | 91.2 |
| Total products | 100 | 100 | 100 | 100 | 100 | 100 | 100 | 100 |
| Parts of Distilled Products per 100 parts of OTP feedstock (including Ex. 10) | | | | | | | | |
| Total useful products | — | 68.2 | 79.6 | 79.9 | 82.7 | 83.8 | 84.4 | 84.8 |
| Total Major by-products | — | 3.3 | 3.1 | 3.2 | 3.6 | 3.8 | 3.9 | 4.0 |
| Saturated OTP | | | | | | | | |
| 2,7-triad DMTs | — | 0.8 | 1.0 | 1.0 | 1.1 | 1.1 | 1.1 | 1.1 |
| Unknown DMT isomer | — | 0.9 | 0.9 | 1.0 | 1.1 | 1.1 | 1.1 | 1.1 |
| Unknown | — | 0.1 | 0.4 | 0.3 | 0.3 | 0.3 | 0.2 | 0.2 |
| Heavies | — | 0.0 | 0.0 | 0.0 | 0.0 | 0.0 | 0.0 | 0.0 |

*the composition of the undistilled total reaction product remaining in the reactor

TABLE 6

| | Initial Reaction Medium | Day No. | | | | | | | | Final Reaction Medium |
|---|---|---|---|---|---|---|---|---|---|---|
| | | 1 | 2 | 3 | 4 | 5 | 6 | 7 | 8 | |
| Feed Rate (g/hr) | | 233 | 233 | 233 | 233 | 233 | 233 | 233 | 233 | |
| Catalyst Charge (g) | | 8.83 | 8.83 | 8.83 | 8.83 | 8.83 | 8.83 | 8.83 | 8.83 | |
| Average Temperature (C.) | | 200 | 200 | 200 | 200 | 200 | 200 | 210 | 210 | |
| Average Pressure (psia) | | 4.4 | 4.0 | 3.7 | 3.6 | 3.6 | 3.6 | 4.3 | 4.3 | |
| Hours on Feed for the Day (hrs.) | | 5.8 | 7.7 | 9.6 | 11.6 | 7.6 | 11.8 | 7.7 | 11.7 | |
| WHSV (g DTP/g cut-hr) | | 26.4 | 26.3 | 26.3 | 25.8 | 26.6 | 25.8 | 26.3 | 26.0 | |
| Wt. of Feed into the Reactor (g) | | 1349 | 1788 | 2235 | 2682 | 1788 | 2682 | 1788 | 2682 | |
| Reactor Contents (g) | 440 | 432 | 403 | 401 | 431 | 470 | 494 | 502 | 512 | 512 |
| | | Cumulative Conditions - End of Day | | | | | | | | |
| Hours on catalyst | | 5.8 | 13.5 | 23.1 | 34.9 | 42.5 | 54.3 | 62.0 | 73.7 | |
| Wt. of Feed into Reactor[1] | | 1781 | 3569 | 5804 | 8486 | 10274 | 12956 | 14744 | 17426 | |
| Wt. Feed/Wt. Catalyst | | 152 | 354 | 607 | 911 | 1113 | 1417 | 1619 | 1923 | |
| Overhead Product Removed | | 1359 | 3166 | 5403 | 8055 | 9804 | 12462 | 14242 | 16914 | |
| | Composition | | | | | | | | | |
| | Initial Reaction | Average Distillate for Day No. | | | | | | | | Final Reaction |

TABLE 6-continued

| Component | Medium | 1 | 2 | 3 | 4 | 5 | 6 | 7 | 8 | Medium |
|---|---|---|---|---|---|---|---|---|---|---|
| OTP | 1.7 | 0.1 | 0.2 | 0.4 | 0.6 | 0.7 | 0.9 | 1.0 | 0.9 | 0.0 |
| 2,6-Triad DMT's and DMN's | 92.8 | 93.9 | 94.9 | 94.8 | 94.6 | 94.5 | 94.3 | 93.7 | 93.8 | 58.9 |
| Sat'd. OTP | 3.0 | 3.3 | 2.5 | 2.5 | 2.4 | 2.4 | 2.4 | 2.8 | 2.8 | 0.8 |
| 2,7-Triad DMT's | 0.9 | 1.2 | 1.1 | 1.1 | 1.1 | 1.1 | 1.1 | 1.1 | 1.1 | 0.5 |
| Heavies | 0.2 | 0.0 | 0.1 | 0.2 | 0.2 | 0.3 | 0.3 | 0.3 | 0.3 | 39.3 |

| | Cumulative Yield of Distillate Component Based on Total Reactor Charge After Day No. | | | | | | | |
|---|---|---|---|---|---|---|---|---|
| Component | 1 | 2 | 3 | 4 | 5 | 6 | 7 | 8 |
| OTP | 0.1 | 0.2 | 0.3 | 0.6 | 0.7 | 0.8 | 0.9 | 0.9 |
| 2,6-Triad DMTs and DMNs | 71.1 | 84.2 | 88.2 | 89.8 | 90.2 | 90.7 | 90.5 | 91.1 |
| Sat'd OTP | 2.5 | 2.2 | 2.3 | 2.3 | 2.3 | 2.3 | 2.7 | 2.7 |
| 2,7-Triad DMTs | 0.9 | 1.0 | 1.0 | 1.0 | 1.0 | 1.0 | 1.1 | 1.1 |
| Heavies | 0.0 | 0.1 | 0.2 | 0.2 | 0.3 | 0.3 | 0.3 | 0.3 |

The reaction conditions employed and the results from Example 18 are presented in Table 6.

From the above description, it is apparent that the objects of the present invention have been achieved. While only certain embodiments and various modifications will be apparent from the above description to those skilled in the art. These alternatives are considered equivalents and are within the spirit and scope of the present invention.

Having described the invention, what is claimed is:

1. An improved method for preparing one or more dimethyltetralins from 5-(o-, m-, or p-tolyl)-pent-1- or -2-ene or 5-phenyl-hex-1- or -2-ene as the alkenylbenzene feedstock, comprising: contacting the feedstock in liquid form with an acidic cyclization catalyst in a suitable reaction zone at a temperature sufficient to provide for the cyclization of the feedstock thereby forming a liquid reaction mixture comprising the cyclization catalyst dispersed in the liquid reaction mixture, one or more dimethyltetralins and a heavy by-product produced during the cyclization reaction wherein (1) when the feedstock comprises 5-(o-tolyl)-pent-1- or -2-ene, at least 80 weight percent of the dimethyltetralin product formed is comprised of 1,5-, 1,6-, 2,5- or 2,6-dimethyltetralin, (2) when the feedstock comprises 5-(m-tolyl)-pent-1- or -2-ene, at least 80 weight percent of the dimethyltetralin product formed is comprised of 1,5-, 1,6-, 1,7-, 1,8-, 2,5-, 2,6-, 2,7- or 2,8-dimethyltetralin or a mixture thereof, (3) when the feedstock comprises 5-(p-tolyl)-pent-1- or -2-ene, at least 80 weight percent of the dimethyltetralin product formed is comprised of 1,7-, 1,8-, 2,7- or 2,8-dimethyltetralin or a mixture thereof, and (4) when feedstock comprises 5-phenyl-1- or -2-hexene, at least 80 weight percent of the dimethyltetralin product formed is comprised of 1,3-, 1,4-, 2,3-, 5,7-, 5,8- or 6,7-dimethyltetralin or a mixture thereof; and removing by distillation from the reaction mixture as overhead a lighter fraction comprising the dimethyltetralin product, wherein the distillation is conducted simultaneously with the addition of the feedstock to the reaction mixture.

2. The method of claim 1 wherein the cyclization catalyst is selected from the group consisting of silicalite catalysts, zeolite beta, acidic ion exchange resins, borosilicate molecular sieves, Mordenite molecular sieves, Y molecular sieves, X molecular sieves, ZSM-5 molecular sieve, phosphoric acid and silica-alumina.

3. The method of claim 1 wherein the temperature of the reaction mixture is in the range of about 120° C. to about 350° C.

4. The method of claim 1 wherein the pressure is in the range of about 0.05 to about 10 atmospheres absolute.

5. The method of claim 1 wherein the amount of feedstock added to the reaction mixture is in the range of about 0.1 to about 100 parts by weight of feedstock per part by weight of acidic cyclization catalyst per hour.

6. The method of claim 1 wherein the lighter fraction removed from the reaction mixture contains less than about 5 weight percent feedstock.

7. The method of claim 1 wherein the feedstock comprises 5(o-toly)-pent-1- or -2-ene.

8. The method of claim 1 wherein the lighter fraction is distilled directly from the reaction zone.

* * * * *

UNITED STATES PATENT AND TRADEMARK OFFICE
CERTIFICATE OF CORRECTION

PATENT NO. : 5,284,987
DATED : Feb. 8, 1994
INVENTOR(S) : David L. Sikkenga, et al It is certified that error appears in the above-indentified patent and that said Letters Patent is hereby corrected as shown below:

| Col. | Line | |
|---|---|---|
| 8 | 15 | "the adsorber water" should read --the adsorbed water-- |
| 10 | 65 | "5:11 weight" should read --5.11 weight-- |

Signed and Sealed this

Twenty-sixth Day of July, 1994

Attest:

BRUCE LEHMAN

Attesting Officer

Commissioner of Patents and Trademarks